United States Patent [19]

Mullens

[11] Patent Number: 4,916,922
[45] Date of Patent: Apr. 17, 1990

[54] RAPID FREEZING APPARATUS

[76] Inventor: Patrick L. Mullens, 2124 Santiago St., Covina, Calif. 91724

[21] Appl. No.: 349,394

[22] Filed: May 9, 1989

[51] Int. Cl.$^4$ .............................................. F25D 3/12
[52] U.S. Cl. ........................................ 62/384; 62/372; 62/388; 62/457.9
[58] Field of Search .................... 62/384, 385, 388 X, 62/372 X, 530, 457.7, 457.9 X

[56] References Cited

U.S. PATENT DOCUMENTS

| | | | |
|---|---|---|---|
| 1,735,082 | 11/1929 | Martin, Jr. .................... | 62/372 X |
| 1,999,670 | 4/1935 | Strouse et al. ................ | 62/384 X |
| 3,373,581 | 3/1968 | Strader ........................ | 62/384 X |
| 3,922,878 | 12/1975 | Jalali (Karchay) .............. | 62/384 |
| 4,134,276 | 1/1979 | Lampard ........................ | 62/457.9 |
| 4,299,429 | 11/1981 | Franklin, Jr. ................. | 62/384 X |
| 4,606,195 | 8/1986 | Winkler ........................ | 62/384 X |
| 4,688,398 | 8/1987 | Baek ........................... | 62/457.9 X |
| 4,766,740 | 8/1988 | Bradley et al. ................. | 62/388 X |
| 4,831,842 | 5/1989 | Kelley et al. .................. | 62/372 X |

Primary Examiner—Lloyd L. King
Attorney, Agent, or Firm—Poms, Smith, Lande & Rose

[57] ABSTRACT

A rapid freezing apparatus utilizes a flexible bag surrounding a cooling chamber for containing solid carbon dioxide formed in situ.

4 Claims, 4 Drawing Sheets

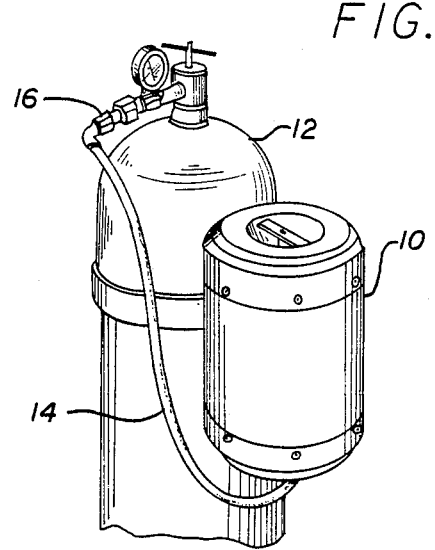
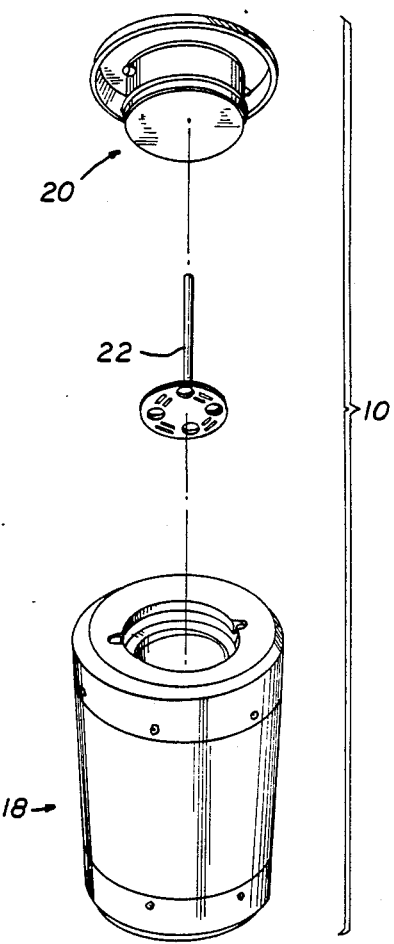
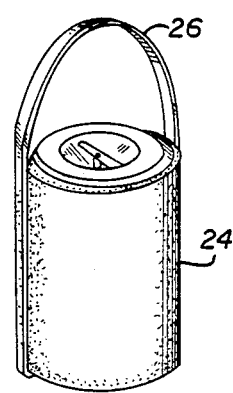
FIG. 1
FIG. 2
FIG. 3

RAPID FREEZING APPARATUS

BACKGROUND OF THE INVENTION

1. Field of the Invention:

This invention relates to the freezing, preservation, storage and transport of samples such as biological samples. In one of its more particular aspects, this invention relates to the rapid freezing of tissue samples for cryostat microtoming and subsequent histopathologic examination. In another aspect, this invention relates to the transport of biological samples under controlled temperature conditions.

In order to examine surgically removed tissues microscopically for the diagnosis of various pathological conditions, it is often necessary to use thin frozen tissue sections. Such thin tissue sections are usually prepared by freezing a tissue sample and then slicing sections from the frozen tissue, for example, by use of a cryostat microtome. Other biological samples frequently must be frozen for purposes of preservation or transport thereof. In addition, low temperature freezing techniques are applicable to nonbiological systems for testing the physical properties of a wide variety of materials.

Advances in frozen section techniques have not paralleled technical advances in every other field of medicine. With each surgical case, pathologist and surgeon will commonly waste critical surgical time waiting for a microscopic diagnosis.

One of the rate limiting factors in microscopic diagnosis is the freezing process. In an attempt to improve upon this frustrating situation, pathologists have tried a wide variety of microtome adaptions and accessories, such as microtome "freezing bars", with limited success.

Low temperature freezing can be accomplished in a number of ways, such as by use of a refrigerator or freezer capable of reducing the temperature of the tissue sample below its freezing point, by spraying the tissue sample with gaseous carbon dioxide or other gas capable of freezing the sample, or by immersing the tissue sample in a suitable mixture of nonaqueous liquid and solid carbon dioxide (dry ice). Each of these methods can be used more or less successfully, but each has its disadvantages.

Use of a refrigerator or freezer is relatively slow. Spraying with a gas is disruptive to the carrying media as well as the tissue and causes irregular freezing of the sample. Additionally, spraying with a gas produces an aerosol effect which is undesirable when working with contaminated or infected tissue specimens. Gaseous $CCl_2F_2$ is potentially toxic and has been implicated as a health hazard and as an environmental pollutant.

Immersion of the sample in a solid $CO_2$-liquid mixture requires the handling of dry ice. Dry ice is depletable, and a continuous source of dry ice is required for subsequent preparations. Probably the most undesirable feature of the dry ice-liquid mixture technique is the violent effervescence which occurs when the dry ice is introduced into the liquid, producing subsequent artifacts of irregular freezing in the carrying media, as well as in the tissue.

In summary, current methodologies are lengthy, time consuming and labor intensive. Additionally, these methods induce various types of mechanical distortion as well as other types of tissue artifact.

2. Prior Art:

Various frozen tissue techniques are described in Waldemar A. Schmidt, *Principles and Techniques of Surgical Pathology*, pp. 117-138 and 145-148, Addison Wesley Publishing Co., Inc. (1983). In particular, this reference describes (at p. 123) the cryostat technique which utilizes a rotary microtome within a cabinet refrigerated to about −20 degrees Celsius. This reference also mentions certain rapid freezing techniques such as the use of liquid nitrogen or isopentane cooled in liquid nitrogen, a slush of dry ice and acetone, the Cryokwik Spray ($CCl_2F_2$) or a freezing attachment using $CO_2$ (p. 128).

U.S. Pat. No. 2,067,676 describes a cooling system which utilizes solid carbon dioxide and a liquid for cooling a body immersed in the liquid.

U.S. Pat. No. 3,176,472 describes a microtome freezing system utilizing thermoelectric freezing by means of a salt brine bath.

U.S. Pat. No. 3,360,943 describes the use of a mixture of dry ice with a liquid such as acetone for the purpose of mechanical testing of metal specimens.

U.S. Pat. No. 3,828,571 describes a particular construction of microtome.

U.S. Pat. No. 3,871,107 describes a freeze dryer which utilizes an aluminum container cooled by snow formed upon the expansion of carbon dioxide gas into the container.

U.S. Pat. No. 3,975,977 describes a microtome with an automatic knife-lowering mechanism.

U.S. Pat. No. 4,004,975 describes a method for cryopreserving human white cells by using a combination of hydroxeythyl starch and dimethyl sulfoxide.

U.S. Pat. No. 4,008,754 describes the use of an inert gas to freeze organs for conservation.

U.S. Pat. No. 4,199,954 describes a method of freezing cells by using a mixture of uranyl acetate and ethyl alcohol.

U.S. Pat. No. 4,224,801 describes a refrigeration unit which is cooled by dry ice mixed with liquid carbon dioxide in a slush tank.

U.S. Pat. No. 4,374,658 describes a machine for making block dry ice.

OBJECTS:

The principal object of the present invention is to provide an apparatus for rapidly cooling samples, including biological samples such as whole blood, serum, plasma and tissues or nonbiological samples.

Another object of this invention is to provide a convenient means for utilizing gaseous carbon dioxide for freezing biological or other samples without exposing the samples to the gaseous carbon dioxide.

Another object of this invention is to utilize a convenient liquid freezing bath without the necessity of handling dry ice.

Yet another object of this present invention is to provide a process for freezing biological or other samples which is more rapid and more convenient than the prior art.

Another object of the invention is to provide rapid freezing without violent effervescence.

Another object of the invention is to provide a rapidly replenishable source of dry ice for use in the freezing process.

Another object is to provide a convenient device for preservation and transportation of biological samples by freezing.

An additional object is to reduce the handling of such biological samples to an absolute minimum, thus eliminating potential sources of mechanical artifact or other forms of biological degradation and allowing optimal diagnostic interpretation.

Other objects and advantages of the present invention will become apparent from the following detailed description.

SUMMARY OF THE INVENTION

The present invention provides an apparatus and process for rapidly freezing biological and other samples. The apparatus utilizes the rapid freezing properties of dry ice and a cooling chamber. In an especially preferred embodiment the cooling chamber may contain a nonaqueous liquid having heat absorbing properties. The apparatus can effect rapid cooling without the inconvenience of handling dry ice and the necessity to replenish the supply of dry ice in mixtures of dry ice and liquid. Specimen preparation time is therefore reduced and the quality of the initial preparation thereby enhanced. In addition, the apparatus can be used to transport frozen samples from location to location while maintaining the optimum environment for the samples.

The apparatus includes a heat conductive cooling chamber and a flexible holder for solid carbon dioxide adapted to receive a stream of gaseous carbon dioxide for conversion into solid carbon dioxide. The holder is also adapted to continuously maintain contact between the solid carbon dioxide within the holder and the exterior surface of the cooling chamber.

The rapid freezing process of the present invention includes the steps of forming solid carbon dioxide in situ chamber in contact with a cooling chamber to cool the chamber to a temperature below the freezing point of a sample to be frozen, which is placed in the chamber. If desired, a heat conductive liquid can be place in the chamber and the sample or samples placed in the cooled liquid for a period of time sufficient to freeze the sample or samples.

BRIEF DESCRIPTION OF THE DRAWINGS

FIG. 1 is a perspective view of a rapid freezing apparatus according to the present invention showing the apparatus connected to a gas cylinder.

FIG. 2 is an exploded perspective view of one embodiment of the rapid freezing apparatus of the present invention.

FIG. 3 is a perspective view of the embodiment shown in FIG. 2 adapted for transport.

DESCRIPTION OF THE PREFERRED EMBODIMENTS

Figure 4:
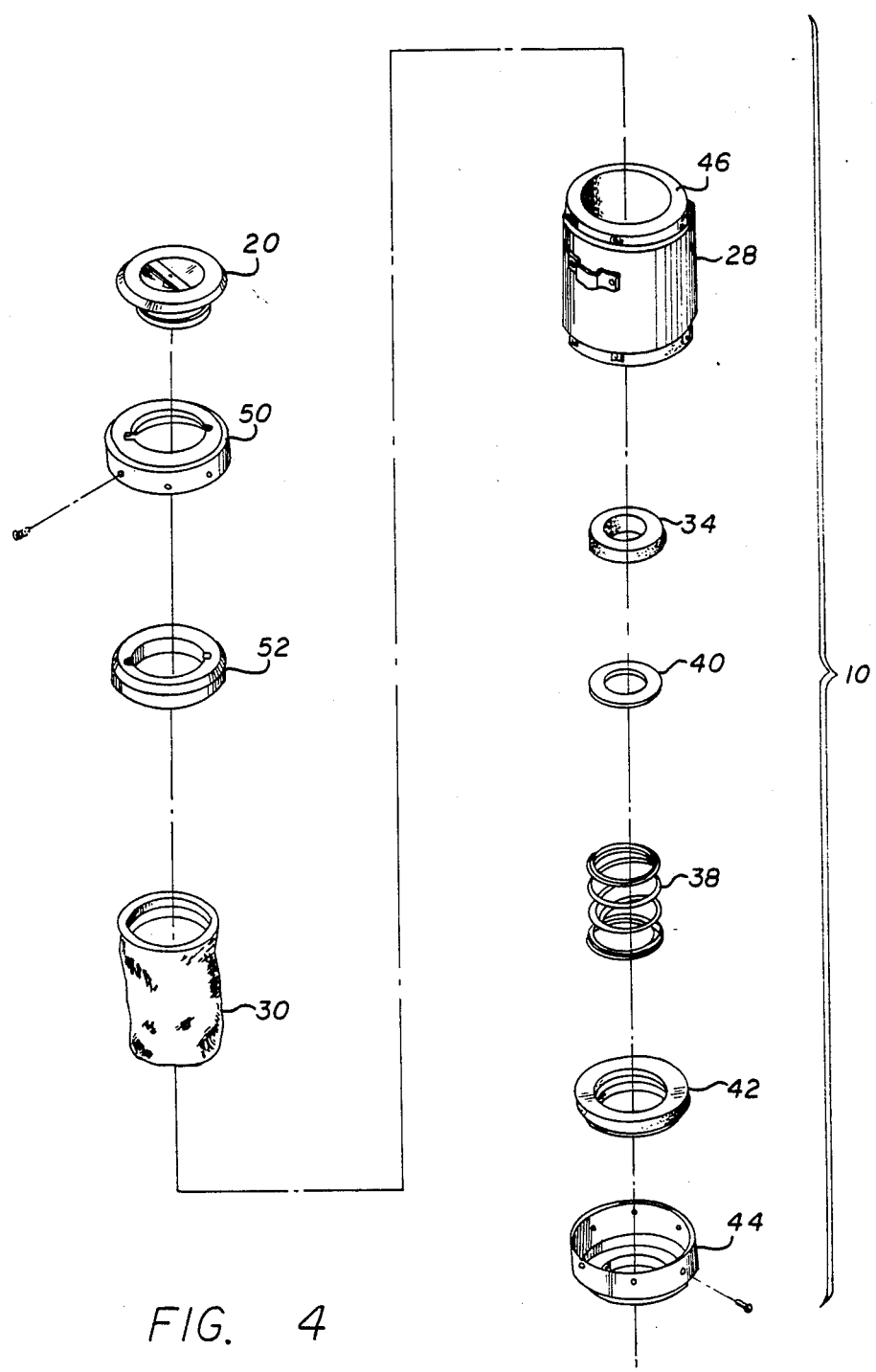
FIG. 4 is a more detailed exploded perspective view of an embodiment of the present invention.

Referring to FIG. 1 of the drawings, the rapid freezing apparatus 10 of the present invention is shown connected to a siphon-equipped carbon dioxide cylinder 12 by means of tubing 14 and a valve 16.

Referring to FIG. 2 freezing apparatus 10 includes a container 18 and a cover 20. Also shown is a sample rack 22, which may be used with the rapid freezing apparatus.

FIG. 3 additionally shows a jacket 24 and a carrying strap 26.

Figure 5:
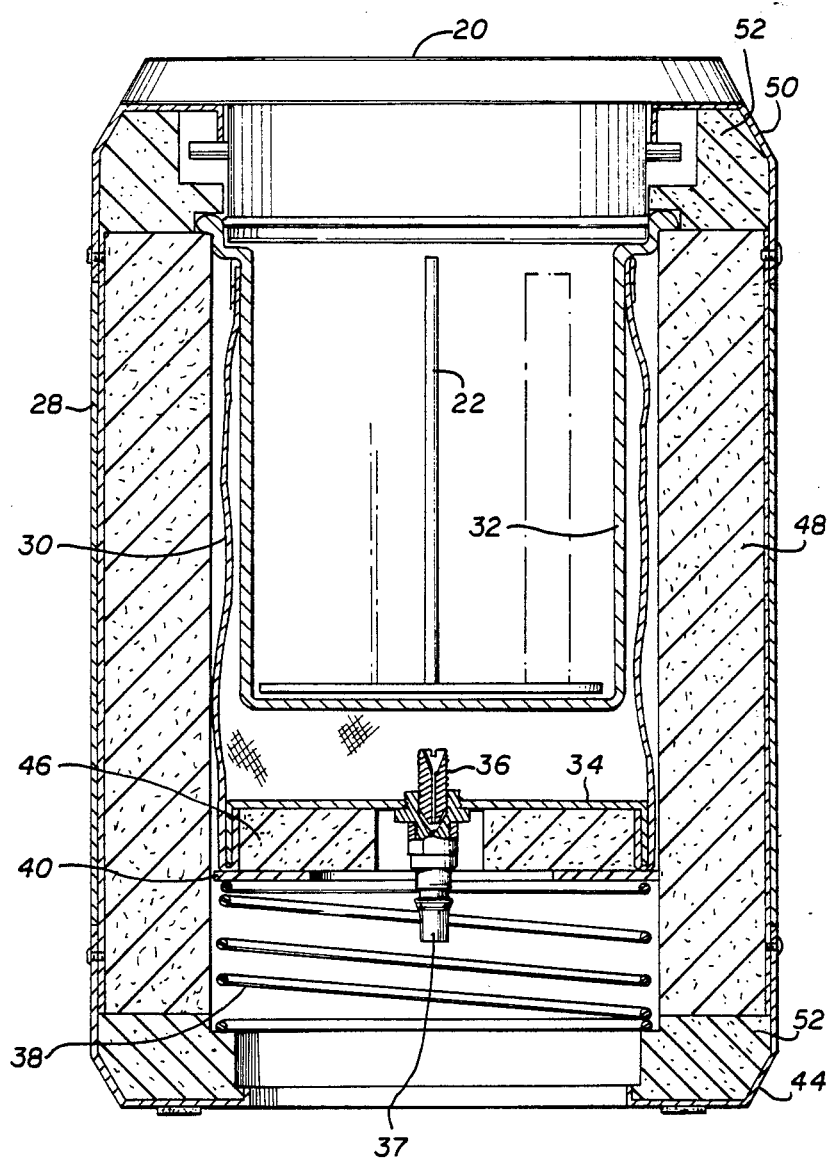
FIG. 5 is a vertical sectional view of an embodiment of the rapid freezing apparatus of the present invention.

The interior structure of one embodiment of a rapid freezing apparatus according to the present invention is shown more particularly in FIGS. 4 and 5.

Within an exterior housing 28 is fitted a sail cloth bag 30 which partially envelopes a cooling chamber 32. Bag 30 is equipped with an insulated rigid base 34 through which projects an injection nozzle 36 with a "quick-disconnect" adapter 37. A spring 38 abuts a spring retaining ring 40 and is seated upon an insulating flange 42. A bottom 44 of exterior housing 28 closes and provides a base for rapid cooling apparatus 10. An insulator 46 is provided adjacent base 34. Insulation 48 is provided interiorly of the outer wall of housing 28. Cover 20 interlocks with a top 50 of exterior housing 28. Insulating flange 52 isolates cooling chamber 32 from top 50.

In operation, carbon dioxide gas from cylinder 12 is introduced into bag 30 through tubing 14 by means of injection nozzle 36. The carbon dioxide gas fills the interior of bag 30 and condenses to form solid carbon dioxide compressing spring 38. Solid carbon dioxide fills the space between bag 30 and cooling chamber 32. When bag 30 is filled with solid carbon dioxide, as evidenced by the downward movement of base 34 and "quick-disconnect" adapter 37, the hose is removed from "quick-disconnect" adapter 37, permitting rapid freezing apparatus 10 to be transported to any selected location.

In order to freeze the desired sample or samples, cover 20 is removed and the sample or samples are placed in cooling chamber 32. If desired, chamber 32 may be filled with a heat conductive liquid and the sample or samples introduced by means of sample rack 22. After the sample or samples have been placed in chamber 32, cover 20 is replaced and locked in position.

If desired, jacket 24 may be placed around the rapid freezing apparatus to provide additional insulation. Carrying strap 26 attached to jacket 24 may be used to transport the rapid freezing apparatus.

Air or various organic fluids can be used in the rapid tissue freezing apparatus of the present invention, for example, acetone, ethyl alcohol, methyl cyclopentane and isobutyl alcohol. (2-methyl Butane) Isopentane, because of its low freezing point of $-159.9$ degrees Celsius and its ready availability is especially preferred.

In practice, most cryostats are held at a constant chamber temperature of $-20$ degrees Celsius since most tissues are cut effectively within 5 degrees Celsius of this temperature. It is generally acknowledged that the optimal temperature of a tissue block when the cryostat chamber temperature is $-20$ degrees Celsius ranges between $-30$ and $-45$ degrees Celsius. With current methodology, it is extremely difficult to bring tissue specimens down to the optimal temperature within a reasonable amount of time. The rapid freezing apparatus of the present invention can bring the tissue to this optimal temperature within a matter of seconds.

Figure 6:
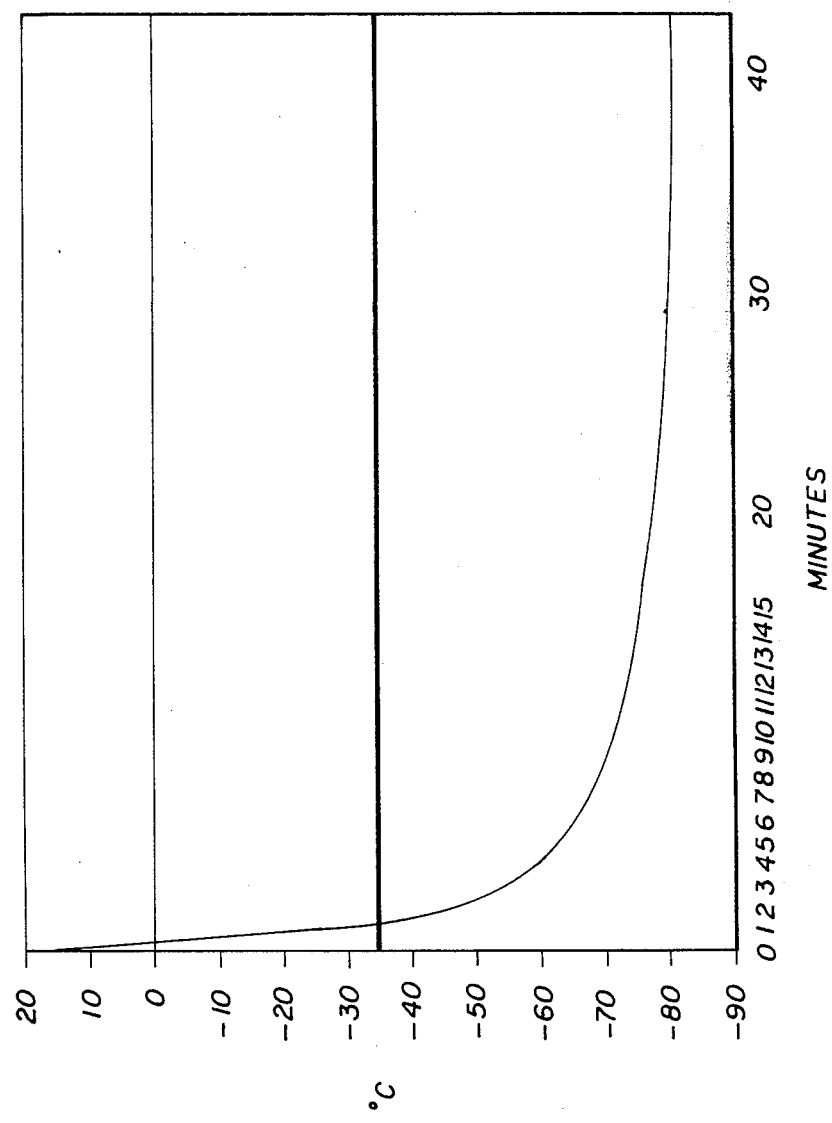
FIG. 6 is a curve showing the temperature response of the rapid freezing apparatus of the present invention.

If the rapid freezing apparatus is maintained at room temperature, an initial "start-up period" of approximately 60 seconds is required to reduce the temperature of the fluid sufficiently ($-30$ to $-45$ degrees Celsius) so that tissuefreezing will occur in several seconds. A typical temperature response curve is shown in FIG. 6. The rapid freezing apparatus utilized to obtain the data plotted in FIG. 4 contained an aluminum heat conductive, fluid container, a non-heat conductive insulating inner shell, and a rigid external housing. It can be seen from FIG. 4 that the optimal freezing range is entered after approximately 60 seconds if the rapid freezing apparatus is kept at room temperature.

In practice, the rapid freezing apparatus is kept at room temperature. Then, each morning, the rapid freezing apparatus is attached to a carbon dioxide bottle equipped with a siphon, and the sail cloth dry ice reservoir is caused to fill with dry ice. When frozen sections are requested in the ensuing several hours, the tissues can easily be prepared one at a time, in tandem, or in multiples. The freezing process in each instance requires only a few seconds once the mounted tissues are placed in the rapid freezing apparatus of the present invention.

Regardless of start-up time intervals, once the dry ice reservoir is filled with dry ice, the rapid freezing apparatus timely reaches temperatures in the −60 to −78 degrees Celsius range. It can be further observed that the temperatures will remain below the minimum optimal freezing temperature of −30 degrees Celsius for a period of approximately 8 hours thereafter. This is an important feature of the present invention, as specimens introduced into the rapid freezing apparatus at any point during this time frame will freeze in seconds.

Over a period of hours, the dry ice in the reservoir is depleted. However, the temperature in the fluid container is held relatively stable (at least in the effective freezing range) by action of the spring which serves to keep dry ice in the reservoir in constant contact with the heat conductive fluid container. Once the dry ice reservoir is completely depleted of dry ice, rapid lowering of the fluid-container temperature can be once again readily accomplished by merely introducing additional gaseous $CO_2$ into the dry ice reservoir.

The temperature of operation of the present apparatus applies over a wide range from −30 degrees Celsius during the initial "start-up period" to −78 degrees Celsius following a period of temperature stabilization. Thus, the present apparatus is designed to provide rapid freezing (within a few seconds) of biological samples in a biologically acceptable temperature range over an extended period of time (8 hours), independent of external power sources.

The invention described above allows smooth, even, quick freezing of a surgical biopsy specimen of almost any size without the production of freezing artifacts inherent in other freezing techniques. A slide preparation which in every way closely approaches the quality of a paraffin block section is thereby produced. The artifactual changes usually seen with other current techniques are essentially absent due to the instantaneous freezing of the specimen at biologically compatible temperatures. No longer does one have to rely upon rapid freezing cryostat attachments which mechanically compress and alter the tissue preparation. The instantaneous freezing process of the present invention produces uniform freezing in all areas of the specimen, no matter how large or how fatty the specimen may be, thereby making practical the freezing of specimens which heretofore have been extremely difficult to evaluate by the frozen section technique.

Another unique design feature of the present invention is the quick disconnect capability. This allows complete portability of the apparatus after it has been charged with solid carbon dioxide.

The foregoing description of the invention has been directed to particular preferred embodiments for purposes of explanation and illustration. It will be apparent, however, to those skilled in the art, that many modifications and changes in the particular design of the apparatus and the materials used therein as well as in the method of use, may be made without departure from the scope and spirit of the invention. It is the applicant's intention in the following claims to cover all such equivalent modifications and changes that fall within the true spirit and scope of this invention.

For instance, it is readily apparent that the temperature response curve could be favorably altered by instituting any of several modifications as follows:

(1) varying the geometry and volume relationships of the heat conductive fluid container;

(2) varying the geometry, volume or surface area of the dry ice reservoir; or (3) providing additional or more sophisticated thermal insulation.

I claim:

1. A portable self-contained apparatus for rapidly cooling samples comprising:

an exterior housing having a peripheral side wall with an inner wall and an outer wall closed off at the top by an insulated cover and at the bottom by an insulated bottom wall having an opening therethrough;

a cooling chamber having a peripheral side wall with an inner wall and an outer wall and an interconnected bottom wall mounted interiorly of said housing open at the top thereof, said open top of said cooling chamber being closed off by said cover;

a flexible collapsible cloth bag mounted in said housing having a flexible and collapsible peripheral side wall mounted between the outer wall of the side wall of said cooling chamber and the inner wall of said housing with insulating means between the peripheral side wall of said bag and the inner wall of said housing, said bag having an insulated generally rigid bottom wall with an exterior wall and an interior wall closing off the bottom thereof disposed between the bottom wall of said cooling chamber and the bottom wall of said housing;

normally closed valve means fluidly communicating the exterior wall of the bottom wall of said bag with the interior wall thereof thereby providing fluid communication through said valve means between the exterior or said housing via the opening in said housing bottom wall and the area between said bag bottom wall and said cooling chamber; and resilient means mounted in said housing disposed between the exterior wall of said bag bottom wall and said housing bottom wall normally biasing said bag bottom wall toward said cooling chamber whereby, when carbon dioxide is introduced through said valve means into the area between said bag bottom wall and said cooling chamber, said bag bottom wall moves downwardly away from said cooling chamber against the bias of said resilient means thereby indicating that the area between said bag and said cooling chamber is filled with carbon dioxide.

2. In the apparatus of claim 1 wherein said bag is of sail cloth.

3. In the apparatus of claim 1 wherein said resilient means is a spring.

4. In the apparatus of claim 1 wherein said valve means has a quick disconnect fitting opening through the exterior wall of said bag bottom wall.

* * * * *